United States Patent [19]

Vera-Castaneda et al.

[11] Patent Number: 4,886,919
[45] Date of Patent: Dec. 12, 1989

[54] PROCESS FOR THE PRODUCTION OF SATURATED NEO-ALCOHOLS

[75] Inventors: Ernesto Vera-Castaneda, Webster; John E. Logsdon, Houston, both of Tex.

[73] Assignee: Union Carbide Chemicals and Plastics Company Inc., Danbury, Conn.

[21] Appl. No.: 125,222

[22] Filed: Nov. 25, 1987

[51] Int. Cl.$^4$ .................... C07C 29/136; C07C 31/12; C07C 31/125
[52] U.S. Cl. .................... 568/885; 568/807; 568/808; 568/809; 568/814; 568/816; 568/822; 568/838; 502/529
[58] Field of Search ............... 568/885, 838, 822, 816, 568/814, 807, 809, 808

[56] References Cited

U.S. PATENT DOCUMENTS

| 2,110,483 | 3/1938 | Guyer | 568/885 |
| 2,322,095 | 6/1943 | Schmidt | 568/885 |
| 2,941,011 | 6/1960 | Hagemeyer et al. | 260/638 |
| 3,201,478 | 8/1965 | Chafetz | 260/618 |
| 4,398,039 | 8/1983 | Pesa et al. | 568/885 |
| 4,532,351 | 7/1985 | Barnett et al. | 568/885 |

FOREIGN PATENT DOCUMENTS

| 433549 | 8/1935 | United Kingdom | 568/885 |
| 994933 | 6/1965 | United Kingdom | 568/885 |
| 1288615 | 9/1972 | United Kingdom . | |
| 1290094 | 9/1972 | United Kingdom . | |

Primary Examiner—J. E. Evans
Attorney, Agent, or Firm—Reynold J. Finnegan

[57] ABSTRACT

A process for the gas phase hydrogenation of unsaturated trisubstituted monoesters to the saturated trisubstituted alcohols using a $Zn_aCu_bX_cNi_dO_e$ reduced catalyst.

7 Claims, 1 Drawing Sheet

PROCESS FOR THE PRODUCTION OF SATURATED NEO-ALCOHOLS

FIELD OF THE INVENTION

This invention relates to a gas phase process for preparing saturated trisubstituted alcohols by the catalytic hydrogenation of unsaturated trisubstituted monoesters.

DESCRIPTION OF THE PRIOR ART

The production of 2,2,4-trimethylpentanol is described in U.S. Pat. No. 2,941,011, issued on June 14, 1960 to H.J. Hagemeyer et al. In this process a saturated 2,2,4-trimethyl-1,3-pentanediol diester is pyrolyzed to its corresponding unsaturated monoester and the unsaturated monoester is then reduced to the saturated 2,2,4-trimethylpentanol. The reduction was carried out over Raney nickel catalyst.

The process disclosed in U.S. Pat. No. 3,201,478, issued on Aug. 17, 1965 to H. Chafetz, differs in the sequence of the reactions. In this patent the first stage involves formation of the saturated diester by esterification of a saturated 1,3-diol. The saturated diester is pyrolyzed in the second stage to the corresponding 2,2,4-trisubstituted unsaturated monoester. This unsaturated monoester is hydrogenated to the saturated monoester in the third stage using catalysts such as Raney nickel, platinum, palladium and copper. In the final fourth stage the saturated ester obtained from the third stage is saponified to the saturated 2,2,4-trisubstituted pentanol using an aqueous base solution at elevated temperature. This reference does not teach the process of the instant invention, namely the hydrogenation of an unsaturated trisubstituted monoester directly to the saturated alcohol.

In Defensive Publication U.S. Pat. No. 880,005, published Nov. 24, 1970, H.J. Hagemeyer et al., the manufacture of 2,2,4-trimethylpentanol by the hydrogenation of an unsaturated 2,2,4-trimethylpentanol monoester is shown using a copper-chromium oxide catalyst. The catalyst used differs from the catalyst herein defined.

Saturated trisubstituted alchols, such as 2,2,4-trimethyl-1-pentanol, have been produced for decades via several different proesses. In British Patent Specification 1,288,615, published Sept. 13, 1972 and issued to B. Yeomans, 2,2,4-trimethyl-1-pentanol is produced by a multi-step process that involves the esterification of 2,2,4-trimethylpentane-1,3-diol with isobutyric acid to produce 3-hydroxy-2,2,4-trimethylpentyl-1 isobutyrate, dehydration of the saturated hydroxyl ester to the unsaturated 2,2,4-trimethylpentenyl-1 isobutyrate, hydrogenation of the unsaturated ester to the saturated 2,2,4-trimethylpentyl-1 isobutyrate over a noble metal hydrogenation catalyst, and saponification of this saturated ester to 2,2,4-trimethyl-1-pentanol. In this reference the 2,2,4-trimethyl-1-pentanol is obtained by the saponification of the ester, not by a reduction process.

Another procedure for the production of 2,2,4-trimethyl-1-pentanol is described in British Specification 1,290,094, published Sept. 20, 1972 and issued to B. Yeomans. The process of this patent involves the transesterification of 2,2,4-trimethylpentane-1,3-diol with 2,2,4-trimethylpentyl-1 isobutyrate using a metal, or an alkoxide, oxide or hydroxide of a Group I or Group II metal. Again, this is not a reduction process. In discussing the prior art the patent mentions that a batchwise hydrogenation process can be used at a pressure of 220 atmospheres of hydrogen at 240° C. for 6 to 12 hours over copper-chromium and zinc catalyst; the referece states this process is costly and gives low selectivity to 2,2,4-trimethyl-1-pentanol (page 1, lines 43 to 49). No other details are given but it is clear from the batchwise procedure used that a liquid phase hydrogenation process is employed not a gas phase process. Further, the specific composition of the catalyst is not clearly disclosed.

SUMMARY OF THE INVENTION

A gas phase process for producing saturated trisubstituted alcohols by the catalytic hydrogenation of unsaturated trisubstituted monoesters in contact with a catalyst cotaining zinc, copper and nickel.

DESCRIPTION OF THE INVENTION

This invention provides a continuous gas phase process for reducing unsaturated 2,2,4-trisubstituted monoesters of general formula I, hereinafter shown, to saturated 2,2,4-trisubstituted alcohols of general formula III, hereinafter shown, at high yields and selectivity.

In the process of this invention the unsaturated trisubstituted monoesters of the structural formula:

and are catalytically hydrogenated in the gas phase to produce saturated trisubstituted alcohols of the structural formula:

wherein R represents the same or different monovalent hydrocarbyl group that can be (i) an alkyl group having from 1 to about 8 carbon atoms, preferably 1 to 4 carbon atoms, (ii) a substituted or unsubstituted cycloalkyl group having 5 or 6 ring carbon atoms, or (iii) an alkaryl or aralkyl group in which the aromatic ring is phenyl or naphthyl, and R' represents hydrogen or a R group.

The unsaturated 2,2,4-trisubstituted monoesters I are known compounds and a method for their production is shown in U.S. Pat. No. 3,408,388, issued to H. J. Hagemeyer et al. on Oct. 29, 1968. Illustrative of such compounds one can mention
2,2,4-trimethylpent-3- enyl isobutyrate,
2-ethyl-2,4-dimethylhex-3-enyl 2-methylbutyrate,
2,2,4-trimethylpent-3-enyl acetate, 2-ethyl,4-dimethylhex-3-enyl acetate,
2-butyl-2,4-diethyloct-3-enyl 2-ethylhexanoate, 2,4-diethyl-2-isobutylhept-3-enyl 2-ethyl-4-methylpentanoate,
2,2,4-trimethylhex-3-enyl 2-ethylbutyrate,
2-cyclohexyl-2,4-dimethylhex-3-enyl 2-cylohexylpropionate,
2,2,4-tricyclohexylbut-3-enyl 2,2-dicylohexylacetate, 2-methyl-2,4-di(p-methylphenyl)pent-3-enyl 2-(p-methylphenyl)propionate, 2,2,4,4-tetra(p-methylphenyl)but-3-enyl 2,2-di(p-methylphenyl)acetate, and similar compounds.

The hydrogenation catalyst suitable for use in the gas phase reaction of this invention comprises the reduced form of an oxides mixture of zinc, copper and nickel with or without other metal atoms which can be represented by the formula:

$$Zn_aCu_bX_cNi_dO_e$$

wherein (a) has a value of about 30 to 75, preferably about 60 to 65;

(b) has a value of about 35 to 60, preferably about 40 to 45;

(c) has a value of about 0 to 15, preferably about 1 to 10;

(d) has a value of from about 0.3 to about 2, preferably 0.5 to about 1.5 and most preferably from about 1 to about 1.5;

(e) has a value sufficient to satisfy the oxygen needs of the metal atoms; that are present in the form of their oxides; and the sum of a +b +c +d plus the trace amounts of other metal atoms present is equal to 100. As indicated one or more other metal atoms X, e.g., aluminum, an alkali metal, preferably potassium, or other metal atoms, can be present in trace amounts that do not deleteriously affect the catalyst. The catalyst can also be used in a liquid phase hydrogenation process, continuous or batch, however, the gas phase hydrogenation process is preferred.

The catalyst is a complex oxides mixture that contains zinc, copper and nickel, and can optionally contain aluminum plus one or more other metal atoms. It may also be supported on an inert carrier, e.g., carbon, if desired. The preferred catalyst contains nickel at a (d) value of from about 1 to 1.5. As shown by Catalyst C in the examples, the conversion of 2,2,4-trimethylpent-3-enyl isobutyrate to 2,2,4-trimethyl-1-pentanol was consistently higher in each series when Catalyst C was used than was the conversion when using any of the other catalysts in the same series. In addition, when the (d) value for nickel was raised to 3, Catalyst D, the higher nickel content did not improve conversion, as shown in the series of experiments for Example 12. Another group of satisfactory catalyst are some of the $Zn_aCu_bAl_cO_e$ complexes, Catalyst A. It was found that the copper chromite catalysts (Catalysts F and G) that do not contain the aluminum. atom and the $Zn_aCu_bNi_dO_e$ catalyst (Catalyst D) that contained a high nickel content, were not satisfactory; lowest conversions in each series generally resulted when these catalysts were used. The zinc-copper-nickel and zinc-copper-nickel-aluminum based catalysts were found best for the gas phase hydrogenation process.

The amount of nickel incorporated into the catalyst seems to be a function of the copper content. There appears to be a critical level of nickel that can be added and it appears to be directly proportional to the amount of copper present, the higher the copper content the more nickel that can be added. For example, for a catalyst with 42 weight percent copper oxide content the maximum nickel oxide content can be about 1.5 weight percent; for a catalyst with a lower copper oxide content of 32.5 weight percent, quantities lower than 1.5 weight percent nickel oxide are required. In general higher levels of nickel oxide, above about 3 weight percent, seem to retard or block the hydrogenation of the double bond. The catalyst is reduced before use, generally better results are obtained when catalyst reduction is performed gradually. This can be accomplished by introducing hydrogen at a concentration of about 0.5 mole percent at a reduced temperature to the oxide catalyst during the catalyst reduction procedure. The temperature and hydrogen concentration are then gradually increased up to a temperature of about 170° C. to avoid formation of hot spots. The hydrogen in and out concentration is monitored during each temperature increase. After a temperature of 170° C. was reached the hydrogen concentration was increased progressively until pure hydrogen was fed to the reactor with continued monitoring of the in and out hydrogen concentration until these values were the same. After the catalyst reduction, the unsaturated 2,2,4-trisubstituted monoester I was fed to the reduced catalyst in the reactor.

The catalytic hydrogenation of the unsaturated trisubstituted monoesters of the structural formula:

and takes place via two routes. In this application the term Formula I includes both isomers. In one reaction route the double bond of the unsaturated ester (I) is hydrogenated to the saturated ester (II):

which is further hydrogenated to make one molecule of the saturated alcohol (III):

and another molecule of the alcohol (IV):

In the other route the unsaturated ester (I) is hydrogenated to one molecule of unsaturated trisubstituted alcohol (V), which inclues both isomers:

and and another molecule of the alcohol (IV):

the unsaturated alcohol (V) is then hydrogenated to the saturated alcohol (III);

All of these reactions occur during the hydrogenation process of this invention.

The reaction is carried out at a temperature sufficient to maintain the reactants in the gas phase, from about 100° C. to about 250° C., preferably from about 150° C. to about 225° C..

The hydrogenation reaction is carried out at a hydrogen pressure of from about 2 atmospheres to about 50 atmospheres or higher, preferably from about 3 atmospheres to about 20 atmospheres.

Theoretically three moles of hydrogen are required to complete the conversion of unsaturated 2,2,4-trisubstituted monoesters I to the saturated alcohol III and other alcohol IV. However, in the reaction an excess of hydrogen is used and the hydrogen to monoester mole ratio can vary from about 5:1 or less to about 500:1 or more. The reaction is carried out under essentially anhydrous conditions. At the conclusion of the hydrogenation, the crude product is refined by conventional procedures, e.g., distillation, and recovered. Unreacted unsaturated 2,2,4-trisubstituted monoesters I and hydrogen are recycled and by-products are recovered.

In this hydrogenation reaction if the unsaturated 2,2,4-trisubstituted monoesters I are not completely hydrogenated, then the unsaturated 2,2,4-trimethylpent-3-enol having a boiling point very close to the boiling point of the saturated 2,2,4-trimethyl-1-pentanol will end-up in the crude final product. The separation of these two compounds by distillation techniques is extremely difficult and refined product containing unsaturated alcohol leads to poor performance in existing end uses, e.g. lubricants. Consequently, catalysts such as those used in the process of this invention that efficiently hydrogenate both the ester group and the double bond are of considerable commercial importance.

The drawing presents the conversions achieved with various catalysts as compared to the catalyst of this invention.

Figure 1:
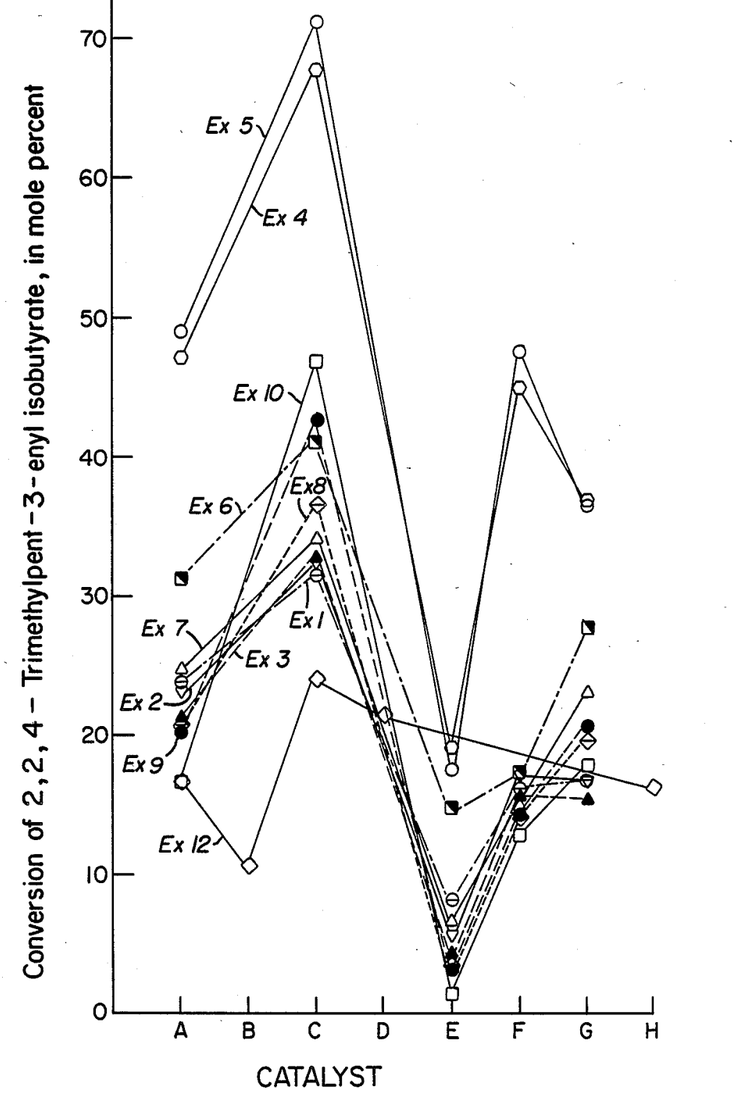

In the drawing the conversions to 2,2,4-trimethylpentanol by the hydrogenation of 2,2,4-trimethylpent-3-enyl monoisobutyrate and its isomer with various catalysts has been graphically plotted. These values are based on the results reported for Example 1 to 12 and the unexpected and unpredictable benefits achieved with Catalyst C of this invention are clearly evident. In each series performed in the examples the Zn 47/Cu 42/Ni 1.5/ Al 9.5 oxides catalyst (Catalyst C) outperformed all of the other catalysts that were compared to it. In preparing this drawing, lines were inserted to connect the values of the different catalysts used in an example; they serve as connecting paths to facilitate comparison of one catalyst to another for that specific example. Thus, for instance, the conversions for Example 5 are 48.96% for Catalyst A, 71.27% for Catalyst C, 17.71% for Catalyst E, 47.59% for Catalyst F and 36.43% for Catalyst G; these points are connected by a line in the drawing.

In Table A, the total conversions of 2,2,4-trimethylpent-enyl isobutyrate isomer for the examples are set forth for each of the catalysts used and which have been plotted in the drawing. The conversion for catalyst C in all examples ranges from about 30% to about 180% higher than the conversion for the other best catalyst in a specific example and from about 250% to about 2,200% higher than the conversion for the worst catalyst in a specific example. Such unexpected superior results could not have been predicted.

| Example | A | B | C | D | E | E | G | H |
|---|---|---|---|---|---|---|---|---|
| 1 | 23.83 | | 31.49 | | 8 | 15.93 | 16.84 | |
| 2 | 20.29 | | 32.39 | | 5.5 | 17.13 | 16.96 | |
| 3 | 21.1 | | 32.19 | | 4.32 | 16.08 | 15.57 | |
| 4 | 47.15 | | 68.04 | | 19.17 | 45.66 | 36.96 | |
| 5 | 48.96 | | 71.27 | | 17.71 | 47.59 | 36.43 | |
| 6 | 31.11 | | 41.17 | | 14.86 | 17.31 | 26.71 | |
| 7 | 24.59 | | 33.93 | | 6.63 | 15.39 | 23.13 | |
| 8 | 20.60 | | 36.77 | | 3.97 | 14.32 | 19.82 | |
| 9 | 20.25 | | 42.86 | | 3.50 | 14.97 | 20.57 | |
| 10 | 16.62 | | 45.18 | | 1.65 | 12.98 | 17.88 | |
| 11 | 2.56 | | 8.25 | | 0.49 | 1.55 | 2.06 | |
| 12 | 16.57 | 10.70 | 24.17 | 21.82 | | | | 16.22 |

The reaction is typically carried out in a continuous reactor loaded with the solid catalyst, which can be in powder, pellet, granular or other form and which can be interspersed with inert materials. The loading of such reactors is known to those of ordinary skill in the art, as are the reactors. The unsaturated trisubstituted monoesters and hydrogen, either premixed or as separate feeds, are continuously fed to the catalyst-packed reactors in the vapor phase and a crude mixture of reaction products is recovered. This crude is then refined by distillation techniques. The use of the catalysts of this invention in the gas phase hydrogenation was shown to give higher selectivity to desired saturated trisubstituted alcohol, higher conversions and essentially no unsaturated trisubstituted alcohol in the product. The formation of unsaturated trisubstituted alcohol is particularly undesirable because of the difficulties encountered in separating it from its saturated counterpart. In a typical reaction unreacted starting materials are recovered and recycled.

The following examples serve to further illustrate the invention. In this application the use of the term 2,2,4-trimethylpent-3-enyl isobutyrate isomers means the isomeric mixture of that compound and 2,2,4-trimethylpent-4-enyl isobutyrate.

The catalyst used in the examples had the following average compositions; weight percent;

Catalyst A: 65 zinc oxide/32.5 copper oxide/1 aluminum oxide

Catalyst B: 65 zinc oxide/32.5 copper oxide/1 aluminum oxide/1.5 nickel oxide/trace potassium carbonate Catalyst C: 47 zinc oxide/42 copper oxide/9.5 aluminum oxide/1.5 nickel oxide/trace potassium carbonate Catalyst D: 46.5 zinc oxide/41 copper oxide/9.5 aluminum oxide/3 nickel oxide/trace potassium carbonate Catalyst E: 65 zinc oxide/32.5 copper oxide/1 potassium carbonate/3 nickel oxide Catalyst F: copper chromite Catalyst G: high activity copper chromite Catalyst H: 47 zinc oxide/42 copper oxide/9.5 aluminum oxide The tubular reactor used in Examples 1 to 12 was a stainless steel double wall tube with the inner tube about 100 cm. long and having an inside diameter of about 0.65 cm, the outer tube had a diameter of about 1.8 cm. The outer tube was equipped with inlet and outlet lines and suitable valves to control introduction of steam for reactor temperature control to provide a uniform shell temperature. The inner tube was equipped with inlet lines for introduction of reactants and exit lines for product recovery and was equipped with needle valves. Temperature measuring means were also placed in the tubular reactor. The inner tube contained about 5 grams of catalyst pellets ranging from about 2 to 6 mm in length and about 3 to 6 mm in diameter evenly distributed with about 0.4 cm by about 3.8 cm long aluminum spacers. The compound to be reduced was fed via a metering pump and mixed with hydrogen before entering the reactor and reduced. The crude product was recovered in a separator immersed in a chilled diethylene glycol bath. The liquid was collected for analysis and unreacted hydrogen gas was removed. A pressure regulator was used to control the feed or reactor pressure; negligible pressure drop along the bed was observed. Heating was effected with 200 psig steam using a steam regulator to control the reactor temperature. The average weight hourly space velocity of the gaseous phase stream of the reactants through the reactor was about 0.2 hr$^{-1}$ to about 1.8 hr$^{-1}$. To assure valid comparisons, high weight hourly space velocities were used in all instances and conversions were intentionally kept low in the examples.

EXAMPLE 1

A Zn/Cu/Al/Ni oxide catalyst was used to reduce 2,2,4-trimethylpent-3-enyl isobutyrate isomers to 2,2,4-trimethyl-1-pentanol. For comparative purposes two others Zn/Cu catalysts and two copper chromite catalysts were also evaluated. Five separate tubular reactors, as described above, were used. The liquid feed of 2,2,4-trimethylpent-3-enyl isobutyrate isomers was fed to a chamber and mixed with hydrogen. This mixture was then used to feed the separate reactors at a feed rate of about 0.104 cc/min of essentially anhydrous 2,2,4-trimethylpent-3-enyl isobutyrate isomers and a hydrogen flow rate of 0.11 cubic foot per minute to each reactor; hydrogen/ester molar ratio of 278:1. The reactor pressure was 59 psig and the temperature was 195° C. The reductions were arbitrarily stopped after five hours; the cold trap temperature being 4° C. A single pass reaction was carried out without any attempt being made to achieve complete hydrogenation to 2,2,4-trimethyl-1-pentanol. As can be seen, hydrogenation to this alcohol, as shown by the weight percent yields attained, are considerably higher when using the catalyst compositions of this invention (Catalyst C) as compared to the other catalysts (Catalysts A, E, F and G) used in the comparative runs. The weight of the crude liquid product recovered from each reactor and its analysis are summarized in Table I.

TABLE I

| Run<br>Catalyst | (i)<br>A | (ii)<br>C | (iii)<br>E | (iv)<br>F | (v)<br>G |
|---|---|---|---|---|---|
| g | 4.525 | 4.535 | 5.129 | 4.791 | 5.332 |
| Yield of crude, g | 31.8 | 30.6 | 38.2 | 29.5 | 43 |
| Anal. of crude, wt. % | | | | | |
| (a) | 13.92 | 13.35 | 2.16 | 9.17 | 9.77 |
| (b) | 74.12 | 65.50 | 87.63 | 81.21 | 80.69 |
| (c) | 0.40 | 11.09 | 4.50 | 0.47 | 0.67 |
| (d) | 1.45 | 0.12 | 0.17 | 0.97 | 0.84 |
| (e) | 6.11 | 5.85 | 0.92 | 3.89 | 3.91 |
| (f) | 4.01 | 4.08 | 4.62 | 4.08 | 4.13 |
| Total conversion of (b), m % | 23.83 | 31.49 | 8.00 | 15.93 | 16.84 |
| Conversion to (a), m % | 21.20 | 20.33 | 3.28 | 13.96 | 14.88 |
| Selectivity, % | 90.44 | 99.13 | 92.46 | 90.28 | 92.00 |

(a) 2,2,4-trimethyl-1-pentanol
(b) 2,2,4-trimethylpent-3-enyl isobutyrate
(c) 2,2,4-trimethylpentyl isobutyrate
(d) 2,2,4-trimethyl-1-pent-3-enol
(e) isobutanol
(f) misc. by-products As can be seen from Table I, the total conversion of 2,2,4-trimethylpent-3-enyl isobutyrate attained with Catalyst C in the process of this invention ranged from about 30% to about 300% greater than the total conversion attained by the use of any of the other catalysts with which is was compared. In addition, the selectivity of 99.13% was considerably higher.

EXAMPLE 2

A series of experiments was carried out of described in Example 1 using essentially the same catalyst compositions, equipment and procedures. In this series the feed rate to each reactor was of a rate of 0.105 cc/min of 2,2,4-trimethylpent-3-enyl isobutyrate isomers and a hydrogen flow rate of 0.112 cubic foot per minute; hydrogen/ester molar ratio of 280:1. The weight of crude liquid product recovered from each reactor and its analysis are summarized in Table II.

TABLE II

| Run<br>Catalyst | (i)<br>A | (ii)<br>C | (iii)<br>E | (iv)<br>F | (v)<br>G |
|---|---|---|---|---|---|
| g | 4.525 | 4.535 | 5.129 | 4.791 | 5.332 |
| Yield of crude, g | 34.5 | 32.6 | 41.6 | 29.8 | 45.2 |
| Anal. of crude, wt. % | | | | | |
| (a) | 11.86 | 13.23 | 1.87 | 9.90 | 10.01 |
| (b) | 77.05 | 64.70 | 90.41 | 78.99 | 80.0 |
| (c) | 0.39 | 12.23 | 2.24 | 0.56 | 0.56 |
| (d) | 1.19 | 0.09 | 0.28 | 0.98 | 0.75 |
| (e) | 4.90 | 5.53 | 0.76 | 4.11 | 3.82 |
| (f) | 4.60 | 4.23 | 4.44 | 5.47 | 4.86 |
| Total conversion of (b), m % | 20.29 | 32.39 | 5.50 | 17.13 | 16.96 |
| Conversion to (a), m % | 18.06 | 20.15 | 2.85 | 15.07 | 15.24 |
| Selectivity, % | 90.76 | 99.32 | 86.81 | 90.87 | 92.90 |

See Table I footnotes (a) to (f)

Table II indicates the total conversion of 2,2,4-trimethylpent-3-enyl isobutyrate attained with Catalyst C ranged from about 50% to about 400% greater than the total conversion attained by the use of the other catalysts with which it was compared. In addition, the selectivity of 99.32% was considerably higher.

EXAMPLE 3

A series of experiments was carried out as described in Example 1 using essentially the same catalyst compositions, equipment and procedures. In this series the feed rate to each reactor was at a rate of 0.106 cc/min of 2,2,4-trimethylpent-3-enyl isobutyrate isomers and a hydrogen/ester molar ratio of 278:1. The weight of crude liquid product recovered from each reactor and its analysis are summarized in Table III.

TABLE III

| Run<br>Catalyst | (i)<br>A | (ii)<br>C | (iii)<br>E | (iv)<br>F | (v)<br>G |
|---|---|---|---|---|---|
| g | 4.525 | 4.535 | 5.129 | 4.791 | 5.332 |
| Yield of crude, g | 12.4 | 11.3 | 15.5 | 10.6 | 16.7 |
| Anal. of crude, wt. % | | | | | |
| (a) | 12.31 | 12.87 | 1.31 | 9.17 | 8.91 |
| (b) | 76.75 | 65.29 | 90.85 | 81.06 | 81.80 |
| (c) | 0.45 | 12.59 | 1.89 | 0.58 | 0.76 |
| (d) | 1.23 | 0.09 | 0.29 | 0.99 | 0.81 |
| (e) | 4.85 | 5.09 | 0.61 | 3.58 | 3.13 |
| (f) | 4.39 | 4.08 | 5.05 | 4.62 | 4.59 |
| Total conversion of (b), m % | 21.10 | 32.19 | 4.32 | 16.08 | 15.57 |
| Conversion to (a), m % | 18.75 | 19.59 | 2.00 | 13.97 | 13.57 |
| Selectivity, % | 90.77 | 99.28 | 81.87 | 90.11 | 91.59 |

See Table I footnotes (a) to (f)

Table III Indicates the total conversion of 2,2,4-trimethylpent-3-enyl isobutyrate attained with Catalyst C ranged from about 50% to about 700% grater than the total conversion attained by the use of the other catalysts with which it was compared. In addition, the selectivity of 99.28% was considerably higher.

EXAMPLE 4

A series of experiments was carried out as described in Example 1 using essentially the same catalyst compositions, equipment and procedures. In this series the feed rate to each reactor was at a rate of 0.0327 cc/min of 2,2,4-trimethylpent-3-enyl isobutyrate isomers and a hydrogen flow rate of 0.0311 cubic foot per minute; hydrogen/ester molar ratio of 250:1. The weight of crude liquid product recovered from each reactor and its analysis are summarized in Table IV.

TABLE IV

| Run<br>Catalyst | (i)<br>A | (ii)<br>C | (iii)<br>E | (iv)<br>F | (v)<br>G |
|---|---|---|---|---|---|
| g | 4.525 | 4.535 | 5.129 | 4.791 | 5.332 |
| Yield of crude, g | 9.2 | 9.7 | 8.2 | 7.8 | 15.3 |
| Anal. of crude, wt. % | | | | | |
| (a) | 28.61 | 30.76 | 6.76 | 27.33 | 22.08 |
| (b) | 49.94 | 29.40 | 77.31 | 50.87 | 60.12 |
| (c) | 0.69 | 21.27 | 7.54 | 0.92 | 0.97 |
| (d) | 1.88 | 0.10 | 0.91 | 2.02 | 1.54 |
| (e) | 14.99 | 15.16 | 3.39 | 14.45 | 11.02 |
| (f) | 3.89 | 3.31 | 4.09 | 4.40 | 4.27 |
| Total conversion of (b), m % | 47.15 | 68.04 | 19.17 | 45.66 | 36.96 |
| Conversion to (a), m % | 45.36 | 46.83 | 10.29 | 41.62 | 33.62 |
| Selectivity, % | 93.74 | 99.67 | 87.91 | 93.01 | 93.37 |

See Table I footnotes (a) to (f)

Table IV indicates the total conversion of 2,2,4-trimethylpent-3-enyl isobutyrate attained with Catalyst C ranged from about 40% to about 250% greater than the total conversion attained by the use of the other catalysts with which it was compared. In addition, the selectivity of 99.67% was considerably higher.

EXAMPLE 5

A series of experiments was carried out as described in Example 1 using essentially the same catalyst compositions, equipmet and procedures. In this series the feed rate to each reactor was at a rate of 0.0342 cc/min of 2,2,4-trimethylpent-3-enyl isobutyrate isomers and a hydrogen flow rate of 0.0304 cubic foot per minute; hydrogen/ester molar ratio of 234:1. The weight of crude liquid product recovered from each reactor and its analysis are summarized in Table V.

TABLE V

| Run<br>Catalyst | (i)<br>A | (ii)<br>C | (iii)<br>E | (iv)<br>F | (v)<br>G |
|---|---|---|---|---|---|
| g | 4.525 | 4.535 | 5.129 | 4.791 | 5.332 |
| Yield of crude, g | 17.3 | 16.5 | 16 | 14.7 | 30 |
| Anal. of crude, wt. % | | | | | |
| (a) | 29.68 | 32.31 | 5.98 | 28.43 | 31.69 |
| (b) | 48.38 | 25.73 | 78.77 | 49.20 | 61.04 |
| (c) | 0.70 | 22.15 | 7.08 | 0.97 | 0.97 |
| (d) | 1.99 | 0.09 | 1.03 | 2.16 | 1.58 |
| (e) | 15.59 | 16.42 | 3.11 | 15.50 | 10.81 |
| (f) | 3.67 | 3.30 | 4.03 | 3.74 | 3.91 |
| Total conversion of (b), m % | 48.96 | 71.27 | 17.71 | 47.59 | 36.43 |
| Conversion to (a), m % | 45.19 | 49.20 | 9.11 | 43.29 | 33.03 |
| Selectivity, % | 93.62 | 99.72 | 85.13 | 92.85 | 93.11 |

See Table I footnotes (a) to (f)

Table V indicates the total conversion of 2,2,4-trimethylpent-3-enyl isobutyrate attained with Catalyst C ranged from about 40% to about 300 percent greater than the total conversion attained by the use of the other catalysts with which it was compared. In addition, the selectivity of 99.72% was considerably higher.

EXAMPLE 6

A series of experiments was carried out as described in Example 1 using essetially the same catalyst compositions, equipment and procedures. In this series the feed rate to each reactor was at a rate of 0.1 cc/min of 2,2,4-trimethylpent-3-enyl isobutyrate isomers and a hydrogen flow rate of 0.1066 cubic foot per minute; hydrogen/ester molar ratio of 280:1. The weight of crude liquid product recovered from each reactor and its analysis are summarized in Table VI.

TABLE VI

| Run<br>Catalyst | (i)<br>A | (ii)<br>C | (iii)<br>E | (iv)<br>F | (v)<br>G |
|---|---|---|---|---|---|
| g | 4.755 | 4.771 | 5.351 | 4.798 | 5.455 |
| Yield of crude, g | 18.3 | 15.7 | 17.5 | 17.5 | 21.1 |
| Anal. of crude, wt. % | | | | | |
| (a) | 18.61 | 17.40 | 5.09 | 9.64 | 14.56 |
| (b) | 67.17 | 56.46 | 81.55 | 79.68 | 71.27 |
| (c) | 0.65 | 14.65 | 6.69 | 1.18 | 2.22 |
| (d) | 1.38 | 0.11 | 0.31 | 0.94 | 1.51 |
| (e) | 7.91 | 7.21 | 1.80 | 3.83 | 5.81 |
| (f) | 4.28 | 4.14 | 4.55 | 4.72 | 4.47 |
| Total conversion of (b), m % | 31.11 | 41.17 | 14.86 | 17.31 | 26.71 |
| Conversion to (a), m % | 28.34 | 26.50 | 7.75 | 14.68 | 22.17 |
| Selectivity, % | 93.01 | 99.36 | 94.10 | 90.97 | 90.46 |

See Table I footnotes (a) to (f)

Table VI indicates the total conversion of 2,2,4-trimethylpent-3-enyl isobutyrate attained with Catalyst C ranged from about 30% to about 240% greater than the total conversion attained by the use of the other catalysts with which it was compared. In addition, the selectivity of 99.36% was considerable higher.

EXAMPLE 7

A series of experiments was carried out as described in Example 1 using essentially the same catalyst compositions, equipment and procedures. In this series the feed rate to each reactor was at a rate of 0.0925 cc/min of 2,2,4-trimetnylpent-3-enyl isobutyrate isomers and a hydrogen flow rate of 0.111 cubic foot per minute; hydrogen/ester molar ratio of 315:1. The weight of crude liquid product recovered from each reactor and its analysis are summarized in Table VII.

TABLE VII

| Run<br>Catalyst | (i)<br>A | (ii)<br>C | (iii)<br>E | (iv)<br>F | (v)<br>G |
|---|---|---|---|---|---|
| g | 4.755 | 4.771 | 5.351 | 4.798 | 5.455 |
| Yield of crude, g | 24.9 | 22.4 | 24.4 | 24.5 | 29.77 |
| Anal. of crude, wt. % | | | | | |
| (a) | 14.45 | 11.67 | 1.58 | 8.82 | 13.03 |
| (b) | 73.32 | 89.01 | 81.27 | 63.16 | 74.71 |
| (c) 0.68 | 16.19 | 3.95 | 0.75 | 1.46 | |
| (d) | 1.24 | 0.09 | 0.20 | 0.79 | 1.19 |
| (e) | 5.86 | 4.59 | 0.56 | 3.39 | 5.09 |
| (f) | 4.45 | 4.30 | 4.70 | 4.99 | 4.51 |
| Total conversion of (b), m % | 24.59 | 33.93 | 6.63 | 15.39 | 23.13 |
| Conversion to (a), m % | 22.0 | 17.76 | 2.40 | 13.43 | 19.85 |
| Selectivity, % | 92.01 | 99.23 | 88.53 | 91.68 | 91.50 |

See Table I footnotes (a) to (f)

Table VII indicates the total conversion of 2,2,4-trimethylpent-3-enyl isobutyrate attained with Catalyst C ranged from about 30% to about 400% greater than the total conversion attained by the use of the other catalysts with which it was compared. In addition, the selectivity of 99.23% was considerable higher.

EXAMPLE 8

A series of experiments was carried out as described in Example 1 using essentially the same catalyst compositions, equipment and procedures. In this series the feed rate to each reactor was at a rate of 0.0952 cc/min of 2,2,4-trimethylpent-3-enyl isobutyrate isomers and a hydrogen flow rate of 0.933 cubic foot per minute; hydrogen/ester molar ratio of 258:1. The weight of crude liquid product recovered from each reactor and its analysis are summarized in Table VIII.

TABLE VIII

| Run<br>Catalyst | (i)<br>A | (ii)<br>C | (iii)<br>E | (iv)<br>F | (v)<br>G |
|---|---|---|---|---|---|
| g | 4.755 | 4.771 | 5.351 | 4.798 | 5.455 |
| Yield of crude, g | 27.7 | 18.8 | 22.6 | 25.3 | 33.2 |
| Anal. of crude, wt. % | | | | | |
| (a) | 11.95 | 11.21 | 0.69 | 8.20 | 11.17 |
| (b) | 76.65 | 59.66 | 91.18 | 82.14 | 77.05 |
| (c) | 0.71 | 19.77 | 2.67 | 0.71 | 1.26 |
| (d) | 1.10 | 0.09 | 0.19 | 0.73 | 1.01 |
| (e) | 5.05 | 4.93 | 0.37 | 3.36 | 4.53 |
| (f) | 4.54 | 4.35 | 4.91 | 4.86 | 4.99 |
| Total conversion of (b), m % | 20.60 | 36.77 | 3.97 | 14.32 | 19.82 |
| Conversion to (a), m % | 18.20 | 17.07 | 1.05 | 12.49 | 17.01 |
| Selectivity, % | 91.48 | 99.23 | 78.51 | 91.71 | 91.58 |

See Table I footnotes (a) to (f)

Table VIII indicates the total conversion of 2,2,4-trimethylpent-3-enyl isobutyrate attained with Catalyst C ranged from about 80% to about 800% greater than the total conversion attained by the use of the other catalysts with which it was compared. In addition, the selectivity of 99.23% was considerable higher.

EXAMPLE 9

A series of experiments was carried out as described in Example 1 using essentially the same catalyst compositions, equipment and procedures. In this series the feed rate to each reactor was at a rate of 0.0939 cc/min of 2,2,4-trimethylpent-3-enyl isobutyrate isomers and a hydrogen flow rate of 0.975 cubic foot per minute; hydrogen/ester molar ratio of 273:1. The weight of crude liquid product recovered from each reactor and its analysis are summarized in Table IX.

TABLE IX

| Run<br>Catalyst | (i)<br>A | (ii)<br>C | (iii)<br>E | (iv)<br>F | (v)<br>G |
|---|---|---|---|---|---|
| g | 4.755 | 4.771 | 5.351 | 4.798 | 5.455 |
| Yield of crude, g | 39.1 | 17 | 27 | 27 | 34.7 |
| Anal. of crude, wt. % | | | | | |
| (a) | 11.68 | 14.53 | 0.64 | 8.60 | 11.59 |
| (b) | 76.70 | 53.70 | 91.64 | 81.46 | 76.49 |
| (c) | 0.65 | 20.80 | 2.26 | 0.67 | 1.28 |
| (d) | 1.17 | 0.09 | 0.18 | 0.78 | 1.07 |
| (e) | 5.04 | 6.65 | 0.37 | 3.58 | 4.90 |
| (f) | 4.76 | 4.23 | 4.90 | 4.90 | 4.67 |
| Total conversion of (b), m % | 20.25 | 42.86 | 3.50 | 14.97 | 20.57 |
| Conversion to (a), m % | 17.79 | 23.13 | 0.98 | 13.10 | 17.65 |
| Selectivity, % | 90.74 | 99.36 | 77.58 | 91.52 | 91.43 |

See Table I footnotes (a) to (f)

Table IX indicates the total conversion of 2,2,4-trimethylpent-3-enyl isobutyrate attained with Catalyst C ranged from about 100% to about 1000% greater than the total conversion attained by the use of the other catalysts with which it was compared. In addition, the selectivity of 99.36% was considerable higher.

EXAMPLE 10

A series of experiments was carried out as described in Example 1 using essentially the same catalyst compositions, equipment and procedures. In this series the feed rate to each reactor was at a rate of 0.0944 cc/min of 2,2,4-trimethylpent-3-enyl isobutyrate isomers and a hydrogen flow rate of 0.948 cubic foot per minute; hydrogen/ester molar ratio of 264:1. The weight of crude liquid product recovered from each reactor and its analysis are summarized in Table X.

TABLE X

| Run<br>Catalyst | (i)<br>A | (ii)<br>C | (iii)<br>E | (iv)<br>F | (v)<br>G |
|---|---|---|---|---|---|
| g | 4.755 | 4.771 | 5.351 | 4.798 | 5.455 |
| Yield of crude, g | 25.6 | 12.1 | 23.4 | 23.6 | 30.2 |
| Anal. of crude, wt. % | | | | | |
| (a) | 9.46 | 13.96 | 0.20 | 7.42 | 10.02 |
| (b) | 79.86 | 51.31 | 93.14 | 82.72 | 79.17 |
| (c) | 0.68 | 24.04 | 1.18 | 0.69 | 1.27 |
| (d) | 1.00 | 0.08 | 0.11 | 0.65 | 0.88 |
| (e) | 3.99 | 6.57 | 0.18 | 3.05 | 4.12 |
| (f) | 5.02 | 4.06 | 5.18 | 5.47 | 4.53 |
| Total conversion of (b), m % | 16.62 | 45.18 | 1.65 | 12.98 | 17.88 |
| Conversion to (a), m % | 14.40 | 21.26 | 0.31 | 11.30 | 15.26 |
| Selectivity, % | 90.31 | 99.41 | 63.82 | 91.88 | 91.83 |

See Table I footnotes (a) to (f)

Table X indicates the total conversion of 2,2,4-trimethylpent-3-enyl isobutyrate attained with Catalyst C ranged from about 180% to about 2,200% greater than the total conversion attained by the use of the other catalysts with which it was compared. In addition, the selectivity of 99.41% was considerable higher.

EXAMPLE 11

A series of experiments was carried out as described in Example 1 using essentially the same catalyst compositions, equipment and procedures except that the reactor temperature was 142° C.. In this series the feed rate to each reactor was at a rate of 0.093 cc/min of 2,2,4-trimethylpent-3-enyl isobutyrate isomers and a hydrogen flow rate of 0.1066 cubic foot per minute; hydrogen/ester molar ratio of 301:1. The weight of crude liquid product recovered from each reactor and its analysis are summarized in Table XI.

TABLE XI

| Run | (i) | (ii) | (iii) | (iv) | (v) |
|---|---|---|---|---|---|
| Catalyst | A | C | E | F | G |
| g | 4.755 | 4.771 | 5.351 | 4.798 | 5.455 |
| Yield of crude, g | 11.7 | 11.9 | 11 | 11 | 14.6 |
| Anal. of crude, wt. % | | | | | |
| (a) | 1.24 | 0.94 | 0.02 | 0.54 | 0.71 |
| (b) | 92.34 | 86.63 | 93.89 | 92.85 | 92.81 |
| (c) | 0.41 | 6.83 | 0.40 | 0.56 | 0.75 |
| (d) | 0.17 | 0.04 | 0.04 | 0.12 | 0.16 |
| (e) | 0.35 | 0.28 | 0.02 | 0.16 | 0.19 |
| (f) | 5.49 | 5.29 | 5.62 | 5.77 | 5.38 |
| Total conversion of (b), m % | 2.56 | 8.25 | 0.49 | 1.55 | 2.06 |
| Conversion to (a), m % | 1.89 | 1.43 | 0.04 | 0.82 | 1.08 |
| Selectivity, % | 88.1 | 96.2 | 39.7 | 82.1 | 81.7 |

See Table I footnotes (a) to (f)

Table XI indicates the total conversion of 2,2,4-trimethylpent-3-enyl isobutyrate attained with Catalyst C ranged from about 220% to about 1600% greater than the total conversion attained by the use of the other catalysts with which it was compared. In addition, the selectivity of 96.2% was considerable higher.

EXAMPLE 12

A series of experiments was carried out as described in Example 1 using essentially the same catalyst compositions, equipment and procedures except the reactor temperature was 190° C.. The catalysts used are identified in Table XII. In this series the feed rate to each reactor was at a rate of 0.12 cc/min of 2,2,4-trimethylpent-3-enyl isobutyrate isomers and a hydrogen flow rate of 0.1 cubic foot per minute; hydrogen/ester molar ratio of 219:1. The weight of crude liquid product recovered from each reactor and its analysis are summarized in Table XII.

TABLE XII

| Run | (i) | (ii) | (iii) | (iv) | (v) |
|---|---|---|---|---|---|
| Catalyst | A | B | C | D | H |
| g | 4.51 | 4.39 | 4.59 | 4.61 | 4.01 |
| Yield of crude, g | 36 | 32 | 34 | 36 | 37 |
| Anal. of crude, wt. % | | | | | |
| (a) | 9.35 | 3.53 | 9.14 | 7.67 | 9.22 |
| (b) | 74.51 | 84.02 | 71.04 | 73.30 | 78.98 |
| (c) | 0.92 | 4.25 | 9.43 | 9.28 | 0.61 |
| (d) | 0.92 | 0.73 | 0.59 | 0.62 | 1.02 |
| (e) | 4.12 | 1.61 | 3.68 | 3.20 | 4.02 |
| (f) | 10.19 | 5.87 | 6.12 | 5.92 | 6.16 |
| Total conversion of (b), m % | 16.57 | 10.70 | 24.17 | 21.82 | 16.22 |
| Conversion to (a), m % | 14.25 | 5.37 | 13.92 | 11.67 | 14.04 |
| Selectivity, % | 90.93 | 82.65 | 93.81 | 92.43 | 89.87 |

See Table I footnotes (a) to (f)

Table XII indicates the total conversion of 2,2,4-trimethylpent-3-enyl isobutyrate attained with Catalyst C ranged from about 10% to about 120% greater than the total conversion attained by the use of the other catalysts with which it was compared. In addition the selectivity of 93.81% was higher.

What is claimed is:

1. A process for production of saturated alcohols of the formula:

by the catalytic hydrogenation of unsaturated monoesters of the formulas:

wherein, when an R group on the enyl group is methyl said unsaturated monoester may include the isomeric form of which comprises hydrogenating said unsaturated monoesters in the vapor phase with hydrogen at a temperature of from about 100° C. to about 250° C. at a pressure of from about 2 atmospheres to about 50° atmospheres in contact with the reduced form of a catalyst consisting of an oxides mixture represented by:

$$Zn_1Cu_bX_cNi_dO_e$$

wherein
(a) has a value of about 30 to about 75,
(b) has a value of about 35 to about 60,
(c) has a value of zero to about 15,
(d) has a value of about 0.3 to about 2,
(e) has a value sufficient to satisfy the oxides needs of the metal atoms, and the sum of (a) plus (b) plus (c) plus (d) is equal to 100, and X is of at least one other metal atom selected from aluminum and alkali metal atoms and wherein R' represents the same or different monovalent hydrocarbyl group selected from (i) an alkyl group having from 1 to about 8 carbon atoms, (ii) an alkyl group having from 1 to about 8 carbon atoms, (ii) a cycloalkyl group having 5 or 6 ring carbon atoms, or (iii) an aryl, alkaryl or aralkyl group in which the aromatic ring is phenyl or naphthyl, and R' is hydrogen or an R group.

2. A process as claimed in claim 1, wherein said saturated alcohol is 2,2,4-trimethylpentanol and said unsaturated monoester is an isomeric mixture of 2,2,4-trimethyl-3-pentenyl isobutyrate and 2,2,4-trimethyl-4-pentenyl isobutyrate.

3. A process as claimed in claim 1 wherein (a) has a value of from about 60 to 65, (b) has a value of from about 40 to 45, (c) has a value of from about 1 to 10, and (d) has a value of from about 0.5 to 1.5.

4. A process as claimed in claim 1, wherein (d) has a value of from about 1 to about 1.5.

5. A process as claimed in claim 1, wherein R is an alkyl group having from 1 to about 4 carbon atoms.

6. A process as claimed in claim 1, wherein the catalyst represented by the formula:

$Zn_{47}Cu_{42}Al_{9.5}Ni_{1.5}O_e$

7. A process as claimed in claim 2, wherein the catalyst represented the by the formula:
$Zn_{47}Cu_{42}Al_{9.5}Ni_{1.5}O_e$

* * * * *

UNITED STATES PATENT AND TRADEMARK OFFICE
CERTIFICATE OF CORRECTION

PATENT NO. : 4,886,919

DATED : December 12, 1989

INVENTOR(S) : Ernesto Vera-Castaneda and John Earle Logsdon

It is certified that error appears in the above-identified patent and that said Letters Patent is hereby corrected as shown below:

Column 1, line 44, "proesses" should read -- processes --.

Column 2, line 1, "referece" should read -- reference --.

Column 2, line 14, "cotaining" should read -- containing --.

Column 4, line 61, "inclues" should read -- includes --.

Column 9, line 31, "experiements" should read -- experiments --.

Column 11, line 3, "2,2,4-trimetnlpent-3-enyl" should read -- 2,2,4-trimethylpentyl-3-enyl --.

Column 11, line 16, Table VII, "(C)0.68" should read -- (C) -- and the data "16.19  3.95  0.75  1.46" should read -- 0.68  16.19  3.95  0.75  1.46 --.

Column 14, line 37, in the formula "$Zn_1$" should read -- $Zn_a$ --.

Column 14, lines 52-53, delete "(ii) an alkyl group having from 1 to about 8 carbon atoms".

Signed and Sealed this

Fourteenth Day of January, 1992

Attest:

HARRY F. MANBECK, JR.

*Attesting Officer*    *Commissioner of Patents and Trademarks*